(12) United States Patent
Hassett

(10) Patent No.: US 6,466,811 B1
(45) Date of Patent: Oct. 15, 2002

(54) DEVICE FOR THE MAPPING OF CARDIAC ARRHYHMIA FOCI

(75) Inventor: James A. Hassett, Bloomington, MN (US)

(73) Assignee: Daig Corporation, Minnetonka, MN (US)

(*) Notice: Subject to any disclaimer, the term of this patent is extended or adjusted under 35 U.S.C. 154(b) by 0 days.

(21) Appl. No.: 09/570,279

(22) Filed: May 12, 2000

Related U.S. Application Data

(60) Provisional application No. 60/133,984, filed on May 13, 1999.

(51) Int. Cl.[7] ................................................. A61B 5/04
(52) U.S. Cl. ........................ 600/374; 600/381; 607/122
(58) Field of Search ................................. 600/373, 374, 600/377, 381, 509, 515, 518; 607/119, 122

(56) References Cited

U.S. PATENT DOCUMENTS

| | | |
|---|---|---|
| 4,332,259 A | 6/1982 | McCorkle, Jr. |
| 4,365,639 A | 12/1982 | Goldreyer |
| 4,641,649 A | 2/1987 | Walinsky et al. |
| 5,127,403 A * | 7/1992 | Brownlee .................. 600/374 |
| 5,156,151 A | 10/1992 | Imran |
| 5,172,694 A * | 12/1992 | Flammang et al. ......... 128/642 |
| 5,228,442 A | 7/1993 | Imram |
| 5,231,995 A | 8/1993 | Desai |
| 5,239,999 A | 8/1993 | Imran |
| 5,263,493 A | 11/1993 | Avitall |
| 5,281,217 A | 1/1994 | Edwards et al. |
| 5,385,146 A | 1/1995 | Goldreyer |
| 5,423,772 A | 6/1995 | Lurie et al. |
| 5,450,846 A | 9/1995 | Goldreyer |
| 5,579,764 A | 12/1996 | Goldreyer |
| 5,755,761 A * | 5/1998 | Obino ....................... 607/122 |
| 5,824,030 A | 10/1998 | Yang et al. |
| 5,921,923 A * | 7/1999 | Kack et al. ................. 600/373 |

FOREIGN PATENT DOCUMENTS

| | | |
|---|---|---|
| CA | 1192263 | 8/1985 |
| EP | 0 373953 | 6/1990 |
| EP | 0 656218 | 6/1995 |
| WO | WO 92/09329 | 6/1992 |

OTHER PUBLICATIONS

Tracy, C.N. "Radio Frequency Catheter Ablation of Ectopic Atrial Tachycardia Using Paced Activiation Sequence Mapping" J. Am. Coll. Cardiol. vol. 21, pp. 910–917 (1993).

Walsh, Edward P. "Ablation of Ectopic Atrial Tachycardia in Children" Radio Frequency Catheter *Ablation of Cardiac Arrhythmias*, Chap. 23 (1994).

K.L. Drake, et al., "Performance of Planar Multisite Microprobes in Recording Extracellular Single–Unit Intracortical Actvity", IEEE Transactions On Biomedical Engineering, vol. 35, No. 9, Sep. 1988, pp. 719–732.

* cited by examiner

*Primary Examiner*—Michael Peffley
*Assistant Examiner*—David M. Ruddy
(74) *Attorney, Agent, or Firm*—Scott R. Cox

(57) ABSTRACT

A device for the mapping of cardiac arrhythmia foci including a catheter body having a distal tip, first and second point electrodes, which are secured to the catheter body and which form a first bipolar pair of electrodes, and third and fourth point electrodes, which are secured to the catheter body and which form a second bipolar pair of electrodes, wherein a line passing between the third and fourth point electrodes is within about 45 degrees of being perpendicular to a line passing through the first and second point electrodes.

23 Claims, 2 Drawing Sheets

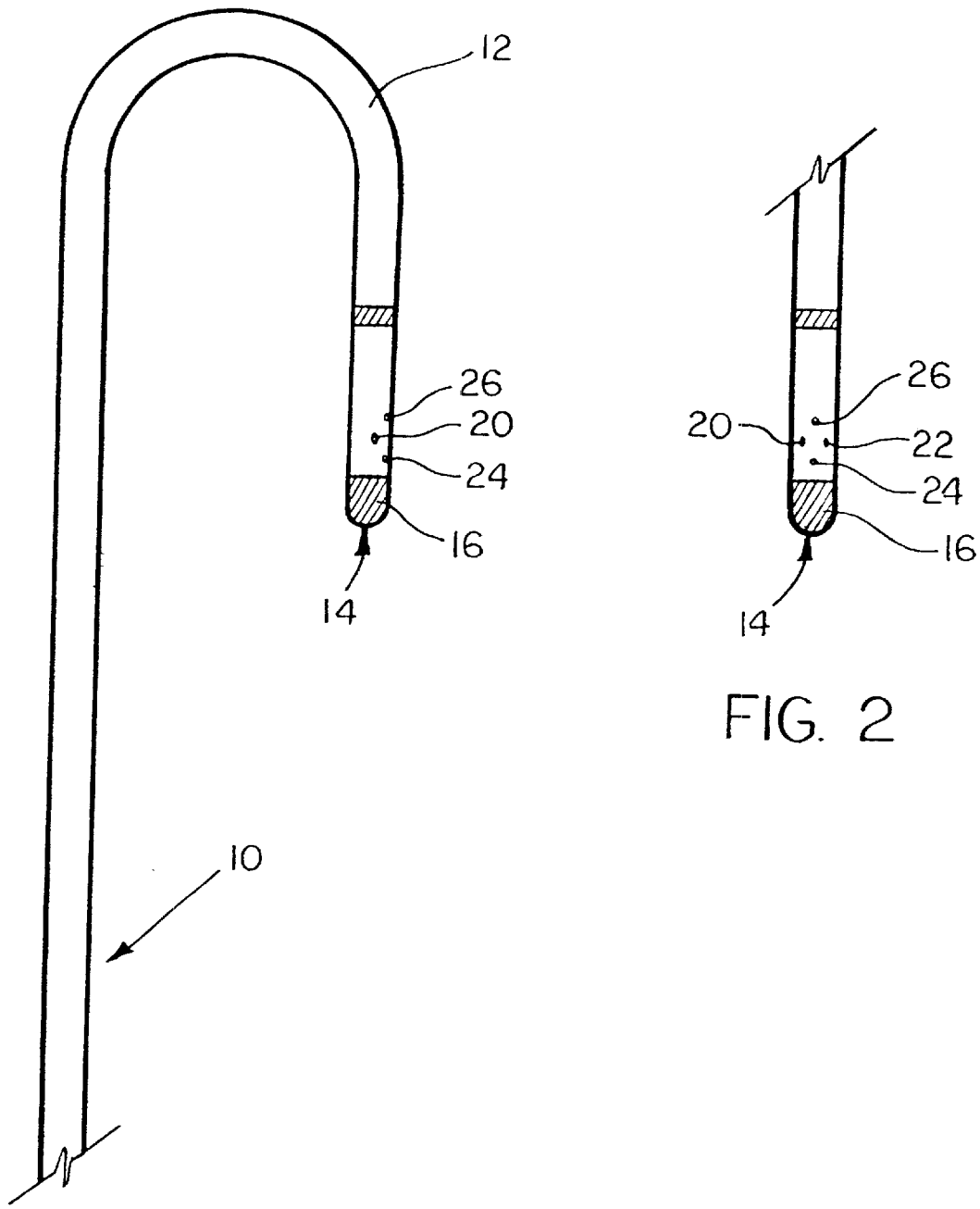

DEVICE FOR THE MAPPING OF CARDIAC ARRHYHMIA FOCI

CROSS REFERENCE TO RELATED APPLICATIONS

This application claims the benefit of U.S. Provisional Application No. 60/133,984, filed May 13, 1999.

BACKGROUND OF INVENTION

1. Field of Invention

This invention relates to a device for the mapping of cardiac arrhythmia foci. In particular, it relates to a catheter containing a grouping of small, non-ring electrodes preferably formed in a diamond shape which form a pair of bipoles on the catheter, which catheter is useful for the mapping of cardiac arrhythmia foci.

2. Prior Art

Catheters have been in use for medical procedures for many years. For example, one use is to convey an electrical stimulus to a selected location within the human body. Another use is to assist in monitoring and measuring electrophysiological activity for diagnostic tests within the human body. Thus, catheters may assist in examination, diagnosis and treatment within a human body while positioned at a specific location, which is otherwise inaccessible without more invasive procedures. In use, catheters are inserted into a vein or artery which is near the body surface. These catheters are then guided to a specific location for examination, diagnosis or treatment by manipulating the catheter through the artery or vein of the human body.

Catheters have become increasingly useful in remote and difficult to reach locations within the body. Catheters are used increasingly for medical procedures involving the human heart. In these procedures a catheter is typically advanced to the heart through veins or arteries and then is positioned at a specified location within the heart. Typically, the catheter is inserted in an artery or vein in the leg, neck, upper chest or arm of the patient and threaded, often with the aid of a guidewire or introducer, and guided through various arteries or veins until the tip of the catheter reaches the desired location in the heart.

Cardiac arrhythmia may be transient or persistent. While most arrhythmias occur in individuals having other forms of underlying heart disease, some arrhythmias occur independently. While atrial arrhythmias do not directly cause death as frequently as ventricular arrhythmias, they increase the risk factor for a number of other diseases such as strokes, thrombosis, atherosclerosis, systemic and cerebral embolism and cause a number of additional medical problems. Atrial fibrillation is the most common sustained heart arrhythmia. It is estimated to occur in upwards of 0.4 percent of the adult population and perhaps as many as 10 percent of the population who are 60 years or older.

Certain patients with symptomatic or life threatening cardiac arrhythmias cannot be adequately treated by drugs or common medical devices, such as defibrillation, or by cardioversion. Other forms of treatment are then mandated, which may include surgery.

Another procedure used for treatment of certain types of cardiac arrhythmia within the last 10 to 15 years is catheter ablation. This procedure has been used to interrupt or modify existing conduction pathways associated with arrhythmias within the heart. The particular area for ablation depends on the type of underlying arrhythmia. One common ablation procedure treats atrioventricular (AV) nodal reentrant tachycardia. With this problem ablation of the fast or slow AV nodal pathways has become an accepted treatment. The use of ablation catheters for ablating locations within the heart has been disclosed, for example in U.S. Pat. Nos. 4,641,649, 5,263,493, 5,231,995, 5,228,442 and 5,281,217.

In addition, catheter ablation for the treatment of ectopic atrial tachycardia is disclosed, for example, in Walsh, Edward P. "Ablation of Ectopic Atrial Tachycardia in Children" *Radio Frequency Catheter Ablation of Cardiac Arrhythmias*, Chap. 23 (1994). See also Tracey, C.N. "Radio Frequency Catheter Ablation of Ectopic Atrial Tachycardia Using Paced Activation Sequence Mapping" J. Am. Coll. Cardial. Vol 21, pp. 910–917 (1993).

The sources of energy used for catheter ablation vary. Initially, high voltage, direct current (D.C.) ablation techniques were commonly used. However, because of problems associated with the use of D.C. current, radio frequency (RF) ablation has become a preferred source of energy for the ablation procedures. Other energy sources also considered for ablation of heart tissue include laser, ultrasound, microwave and fulgutronization.

Ablation of a precise location within the heart, such as a focus of a cardiac arrhythmia, requires the precise placement of the ablation catheter within the heart. Precisely positioning the ablation catheter is especially difficult because of the physiology of the heart, particularly as the ablation procedures generally occur while the heart is beating. Commonly, the placement of the catheter is determined by a combination of electrophysiological guidance and fluoroscopy (placement of the catheter in relation to known features of the heart which are marked by radiopaque diagnostic catheters which are placed in or at known anatomical structures such as the coronary sinus, high right atrium and the right ventricle).

Accordingly, the treatment of cardiac arrhythmias has increasingly been dependent upon the ability to identify the precise location or origin in the heart of the abnormal rhythm. The prior art practice for locating an abnormal rhythm is to place a catheter within the heart carrying a standard array of ring and/or tip electrodes. Direct contact of the tip electrode with the cardiac tissue is used for making an intracardiac electrogram in a manner similar to that has been practiced for many years with respect to pacemaker sensing. See, for example, U.S. Pat. Nos. 5,156,151 and 4,365,639.

A relatively new process for sensing arrhythmia within a heart utilizes one or more pairs of circumferential, orthogonal sensing electrodes, such as are disclosed in U.S. Pat. No. 4,365,639. See also Canadian Patent No. 1,192,263. A series of circumferential orthogonal electrodes located in pairs around the body of a catheter are disclosed in U.S. Pat. Nos. 5,385,146, 5,450,846 and 5,579,764. These patents disclose a process whereby a pair or a series of pairs of circumferential orthogonal electrodes are used in conjunction with an ablation or pacing catheter simultaneously to sense electrophysiological activity in the heart and to pace or ablate predetermined locations in the heart. Only localized cardiac signals at precise locations within the cardiac tissue of the heart immediately adjacent to the predetermined location where the orthogonal electrodes are positioned are sensed by the orthogonal electrode pairs. The specific design and arrangement of these orthogonal electrode pairs limits their use within the heart to simultaneous sensing and pacing or ablating activities. While the procedures disclosed by these patents are quite useful once the focus of the cardiac arrhythmia has been determined, it is necessary to first identify the general location of the arrhythmia focus within the cardiac tissue.

Accordingly, it is an object of the invention to disclose a product for the mapping of cardiac tissue to disclose the location of cardiac arrhythmia foci.

It is a further object of the invention to disclose a catheter containing a plurality of point electrodes which form a pair of bipoles for the sensing of the direction of an activation wave generated by cardiac arrhythmia foci as the wave passes the pair of bipoles.

It is a still further object of the invention to disclose a catheter for the sensing of the direction of an activation wave generated by cardiac arrhythmia foci in the heart as the wave passes a pair of bipoles secured to the catheter, wherein the bipoles are formed from two pair of point electrodes formed in a diamond shape.

It is a still further object of the invention to disclose a catheter containing a plurality of point electrodes formed in a pattern which is capable of sensing the activation wave from an ectopic atrial tachycardia and other forms of cardiac arrhythmia focus within the heart.

It is a still further object of the invention to disclose a process for the mapping of cardiac arrhythmia focus in the heart by use of a catheter containing a plurality of point electrodes forming at least two bipoles, wherein the bipoles are preferably about 90 degrees apart from each other.

These and other objects can be obtained by the disclosed process for the treatment of cardiac arrhythmia focus and design of a catheter containing a pair of bipoles for use with that process which are disclosed by the instant invention.

SUMMARY OF INVENTION

The present invention is a catheter for sensing electrophysiological activity within a human heart comprising:
an elongated catheter body having a distal tip,
a first and second point electrodes which are secured to the elongated catheter body comprising a first bipolar pair of electrodes, and
third and fourth point electrodes which are secured to the catheter body comprising a second bipolar pair of electrodes, wherein a line passing between the third and fourth point electrodes is within about 45 degrees of being perpendicular to a line passing through the first and second point electrodes.

Preferably, these four point electrodes are formed in a diamond-shaped pattern and preferably the distance between each adjacent point electrode is approximately the same.

The present invention also includes a catheter for sensing electrophysiological activity within a human heart comprising
an elongated catheter body having a distal tip,
a first and second point electrode which are secured to the elongated catheter body, comprising a first bipolar pair of electrodes,
third and fourth point electrodes which are secured to the catheter body comprising a second bipolar pair of electrodes, wherein a line passing between the third and fourth point electrodes is within about 45 degrees of being perpendicular to a line passing through the first and second point electrodes, and
a unipolar electrode secured to the distal tip of the catheter body.

Preferably, these four point electrodes are formed in a diamond-shaped pattern and preferably the distance between each adjacent point electrode is approximately the same.

The present invention also includes a catheter for sensing electrophysiological activity within a human heart comprising
an elongated catheter body having a distal tip,
a first and second point electrode which are secured to the elongated catheter body, comprising a first bipolar pair of electrodes, and
a third point electrode which is secured to the catheter body at a location distal from either of the first and second point electrodes which operates with the second point electrode to form a second bipolar pair of electrodes, wherein a line passing between the first and second point electrodes is generally perpendicular to a line passing between the second and third point electrodes.

The present invention also includes a process for the mapping of cardiac arrhythmia focus activity within a heart comprising
introducing a catheter within a chamber of the heart, wherein the catheter comprises an elongated catheter body having a distal tip, first and second point electrodes which are secured to the elongated catheter body and which comprise a first bipolar pair of electrodes, and third and fourth point electrodes which are secured to the catheter body comprising a second bipolar pair of electrodes, wherein a line passing between the third and fourth point electrodes is within about 45 degrees of being perpendicular to a line passing through the first and second point electrodes,
sensing signals in heart tissue using the first and second bipolar pairs of electrodes to determine the general location of the cardiac arrhythmia focus within the heart, and
determining the precise location of the cardiac arrhythmia focus using a unipole electrode secured to the catheter body.

BRIEF DESCRIPTION OF THE DRAWINGS

FIG. 1 is a side view of the catheter of the invention showing the point electrodes from the side of the catheter.

FIG. 2 is a view of the catheter of FIG. 1 rotated 90 degrees showing the four point electrodes arranged in a diamond shape near a distal end of the catheter.

DETAILED DESCRIPTION OF THE PREFERRED EMBODIMENT

Figure 3:
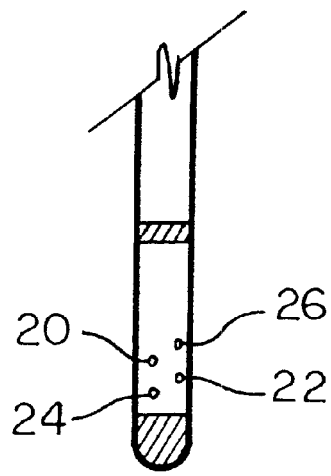
FIG. 3 is an alternative arrangement of the point electrodes near the tip of the catheter.

A typical human heart includes a right ventricle, a right atrium, left ventricle and left atrium. The right atrium is in fluid communication with the superior vena cava and the inferior vena cava. The atrioventricular septum separates the right atrium from the right ventricle. The tricuspid valve contained within the atrioventricular septum communicates the right atrium with the right ventricle. On the inner wall of the right atrium where it is connected with the left atrium is a thin walled, recessed portion, the fossa ovalis. Between the fossa ovalis and the tricuspid valve is the opening or ostium for the coronary sinus. The coronary sinus is the large epicardial vein which accommodates most of the venous blood which drains from the myocardium into the right atrium.

In a normal heart, contraction and relaxation of the heart muscle (myocardium) takes place in an organized fashion as electro-chemical signals pass sequentially through the myocardium from the sinoatrial (SA) node to the atrialventricular (AV) node and then along a well defined route which includes the His-Purkinje system into the left and right ventricles. Initial electric impulses are generated at the SA node and conducted to the AV node. The AV node lies near the ostium of the coronary sinus in the interatrial septum in the right atrium. The His-Purkinje system begins at the AV node and follows along the membranous interatrial septum toward the tricuspid valve through the atrioventricular septum and into the membranous interventricular septum. At about the middle of the interventricular septum, the His-Purkinje system splits into right and left branches which straddle the summit of the muscular part of the interventricular septum.

Sometimes abnormal rhythms occur in the heart which are referred to as arrhythmia. Three of the most common arrhythmia are ectopic atrial tachycardia, atrial fibrillation and atrial flutter. Abnormal rhythms sometimes originate from a single point of cardiac tissue which are called cardiac foci.

One type of arrhythmia focus is ectopic atrial arrhythmia ("EAT"). EAT is a cardiac rhythm disorder that involves rapid impulse generation from a single atrial focus outside the sinoatrial node. In many circumstances EAT may occur for long periods of time, possibly leading to cardiomyopathy. Because EAT is one of the few reversible causes of cardiomyopathy, more effective treatment of EAT is sought. Radio frequency ablation for the treatment of EAT is disclosed in Walsh, Edward P., "Ablation of Ectopic Atrial Tachycardia in Children," *Radio Frequency Catheter Ablation of Cardia Arrhythmias*, Chap. 23 (1994). See also Tracey, C.N. "Radio Frequency Catheter Ablation of Ectopic Atrial Tachycardia Using Paced Activation Sequence Mapping" J. Am. Coll. Cardiol. Vol 21, pp. 210–917 (1993).

While pharmacological treatments are sometimes effective in the treatment of cardiac arrhythmia, in some circumstances drug therapy is ineffective and frequently is plagued with side effects, such as dizziness, nausea, vision problems and other difficulties.

In the last few years surgical procedures have also been utilized in the treatment of some arrhythmia. The goal of these surgical procedures parallels that of the pharmacological treatments, to relieve both the subjective symptoms of arrhythmia as well as to normalize hemodynamics by restoring regular atrial contributions to the cardiac output.

The ablation catheters used to perform the ablation procedures produce scar tissue at the selected site or location within the heart. The energy necessary to scar or ablate the tissue can be provided from a number of different sources. Originally direct current was utilized to provide the energy for ablation procedures. More recently the preferred choice of energy source has been radio frequency energy (R.F.). Laser, microwave, ultrasound, low and high energy direct current and fulgutronization procedures have also been utilized to perform ablation procedures. The preferred source of energy for the ablation procedures of the instant invention is R.F. energy.

Significant difficulties in performing any cardiac procedure in the heart are caused by the physiology of the heart itself when beating, especially if that beating is abnormal. The preferred procedure for the treatment of arrhythmia requires the precise positioning and contact pressure of the ablation catheter within the heart to ablate a predetermined location of the arrhythmia. Mere introduction of an ablation catheter into the heart without precise placement will not be sufficient to satisfactorily ablate the desired location.

An element in the treatment of these arrhythmia also includes sensing the location of arrhythmia focus in the heart to efficiently and accurately map the cardiac tissue. The physiology of the heart and its beating also interferes with the effectiveness of sensing catheters.

Medical practitioners often monitor the introduction of cardiac catheters and their progress through the vascular system by use of fluoroscopes. Unfortunately, fluoroscopes can not easily identify specific features in the heart, in general, and the critically important structures of the various chambers of the heart in specific, thus making placement and utilization of an ablation catheter extremely difficult. This placement is especially difficult as the beating heart is in motion, resulting in the catheter moving within the heart as blood is being pumped through the heart. The specially designed catheter of the present invention addresses and solves some of these problems by assisting in the placement of the ablation catheter for accurate ablation procedures.

The catheter (10) of the present invention is utilized to sense electrophysiological activity within a human heart and is generally comprised of a conventional elongated catheter body (12) having a distal tip (14) as shown in FIGS. 1 and 2. The catheter body can be conventional, produced from conventional catheter materials. Secured near the distal end of the catheter (10) is a plurality of point electrodes (20, 22, 24, 26), preferably at least two pair of these point electrodes, as shown in FIGS. 1 and 2. The first and second electrodes (20, 22) are secured to the elongated catheter body (12) and operate as a first bipolar pair of electrodes. These two point electrodes are wired conventionally to form a first bipole and are attached to a conventional sensing apparatus, such as amplifiers, to sense electrocardiac signals from throughout the heart. The bipole is operably interfaced with conventional differential receiving and processing equipment to provide directional vectors to the origin of electrophysiological activity of the heart.

These point electrodes, sometimes referred to as bead electrodes or dot electrodes, are conventional small electrodes and may be formed in any circular, rectangular, square or non-regular shape. The overall distance across the outside surface of these point electrodes is not critical and is preferably from about 0.1 mm. (0.004 inch) to about 2.0 mm. (0.08 inch). These point electrodes are preferably not conventional tip electrodes or ring electrodes.

The first pair of point electrodes (20, 22) are located a sufficient distance apart so that they form an effective bipole. Preferably, the first pair of point electrodes are at least about 0.5 mm. (0.02 inch) apart and more preferably from about 0.5 mm. (0.02 inch) to about the overall width of the catheter body (12) apart as shown in FIG. 2.

The first pair of point electrodes (20, 22) may be secured to the catheter body (12) longitudinally, i.e., circumferentially located on the catheter body (12), or they may be placed at various oblique angles away from a circumferential location, as shown for example in FIG. 3. Depending upon the diameter of the catheter body (12) and the angle that the first and second point electrodes (20, 22) form in relation to the catheter body (12), the distance between the first and second point electrodes may vary from a minimum of about 0.5 mm. (0.02 inch) to the maximum diameter of the catheter shaft. Typically, the largest catheter diameter used for this type of procedure is a 12 French or 4.0 mm. (0.16 inch) while typically the smallest catheter diameter is 4 French (1.3 mm.) (0.05 inch). Thus, the distances between these first and second point electrodes may vary from a minimum of about 0.5 mm. (0.02 inch) to a maximum of about 4.0 mm. (0.16 inch).

The use of bipolar electrodes for sensing has been taught in the prior art, such as, for example, in U.S. Pat. No. 5,385,146 but only when formed as circumferential, orthogonal electrodes. The present invention discloses the use of a pair of bipole electrodes formed with particular designs which are not and need not be circumferentially located on the catheter body.

The second pair of electrodes (24, 26) form the second bipole on the catheter. The second pair of point electrodes (24, 26) as shown in FIG. 2 are rotated away from the position of the first pair of point electrodes (20, 22). Preferably a line formed between the third and fourth point electrodes (24, 26) when compared with a line formed between the first and second electrodes (20, 22) is at least about 30 degrees apart, preferably 45 degrees and most preferably about 90 degrees apart as shown in FIG. 2.

It is not necessary that any of the pairs of point electrodes be longitudinally circumferential as shown, for example, in FIG. 3. One important aspect of the invention is that the pairs of bipoles be at least about 30 degrees apart from each other and preferably 45 to 90 degrees apart as shown in FIG. 2. By the placement of the point electrodes (20, 22, 24, 26) in a relatively perpendicular position as shown in FIG. 1, the output of the bipoles can be compared electronically to determine from which general direction relative to the four electrodes the arrhythmia signal has been generated. By comparing the signals sensed by the first and second bipoles, the clinician can determine with a significant degree of specificity the direction from which the arrhythmia signal has been generated and thus determine the source of the electrical activity of the arrhythmia on the cardiac tissue. However, no specific location for the arrhythmia focus in generally possible from an initial reading of the bipoles because of variations in the time of passage and the direction of passage of the activation wave through the cardiac tissue from the arrhythmia focus.

While the bipolar pair of point electrodes (20, 22, 24, 26) as disclosed in the invention are particularly helpful in determining the general area of the arrhythmia focus on the cardiac tissue, preferably a unipolar tip electrode (16) is secured at the distal tip (14) of the catheter body (12) to operate in conjunction with an extracardiac electrode (not shown) to determine the precise location of the arrhythmia focus. The extracardiac electrode is preferably a conventional electrode secured at a position which is significantly proximal from the most proximal of the point electrodes. Preferably the extracardiac electrode is located from about 17 cm. (6.7 inch) to about 35 cm. (13.8 inch) proximal from the most proximal of the point electrodes. Conventional ring electrodes may also be secured to the catheter body but are not generally used for this bipolar sensing procedure. In addition, the tip electrode (16) secured to the distal tip (14) of the catheter body (12) may function solely as a diagnostic tip, or alternatively, it may operate as a sensing and ablation electrode.

Figure 4:
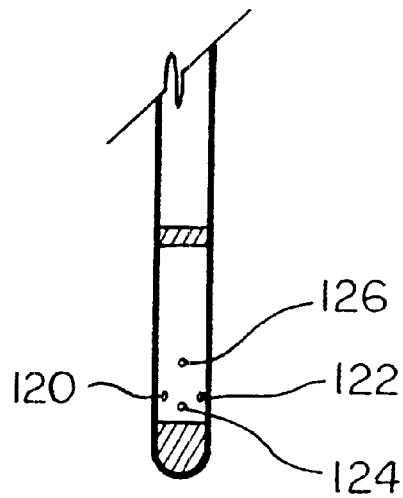
FIG. 4 is a further alternative arrangement for the point electrodes of the catheter.
Figure 5:
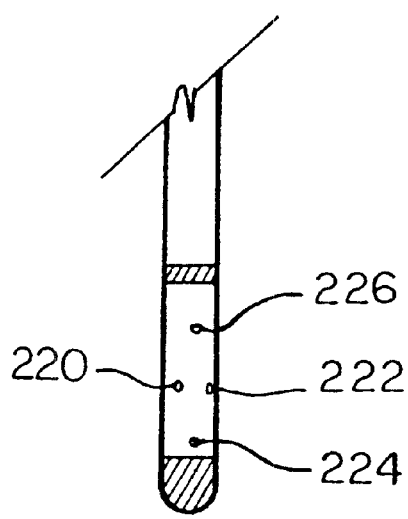
FIG. 5 is a further alternative arrangement of the point electrodes of the catheter.

The particular placement of the first bipolar pair of electrodes (20, 22) in relation to the second pair of bipolar electrodes (24, 26) can be modified as required by the user of the product. While the distance between each of the point electrodes (20, 22, 24, 26) is preferably approximately the same, i.e., within about 2.0 mm. (0.08 inch) and preferably from about 0.3 mm. (0.01 inch) to about 0.6 mm. (0.02 inch) apart, that distance may be varied depending upon the user of the product. For example, the distal-most electrode (124) of the second bipole may be moved closer to the space between the first and second point electrodes (120, 122) as shown, for example, in FIG. 4. In addition, the distance between the third and fourth point electrodes (224, 226) may be greater than the distance between the first and second point electrodes (220, 222), as shown in FIG. 5.

Figure 6:
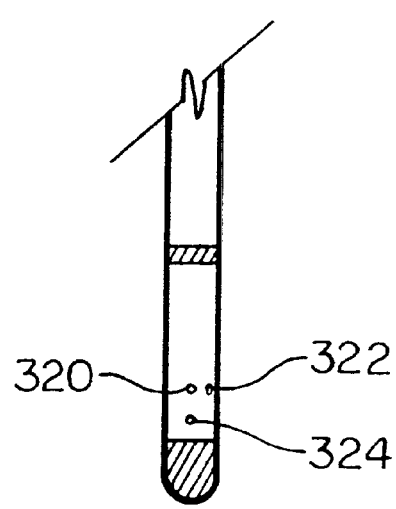
FIG. 6 is a further alternative arrangement of the point electrodes of the catheter.

In an alternative embodiment, the first bipole is formed by placing the first and second point electrodes (320, 322) as shown in FIG. 6 in the same position as the first and second point electrodes (20, 22) as shown in FIG. 1. The second bipole is formed by a single third point electrode (324), which operates in conjunction with the second electrode (322) to form the second bipole. In this combination, the first bipole is formed by the interaction of the first and second point electrode (320, 322) while the second bipole is formed by the interaction of the second and third point electrodes (322, 324). The angle formed by the line between the first and the second point electrodes (320, 322) and the line between the second and the third point electrodes (322, 324) may vary from about 45 degrees to about 135 degrees, preferably from about 60 to 120 degrees and most preferably around 90 degrees as shown in FIG. 6.

Processing of the signals generated by the first and second bipoles may be accomplished by conventional equipment which is well known to those skilled in the art. Based on the placement of the point electrodes on the catheter, the location of the signal from the arrhythmia focus can be generally determined. Precise location of the arrhythmia focus is difficult because the activation wave may pass through the cardiac tissue in a direct line from the arrhythmia focus point to the bipolar pair of electrodes. Once the general area of the arrhythmia focus is determined, the tip electrode (16) is activated as a unipolar electrode with an extracardiac electrode (not shown) to precisely localize the source of the arrhythmia. Once the particular location of the arrhythmia focus within the heart is determined, the tip electrode (16) may then be utilized as an ablation electrode, preferably utilizing radio frequency energy. Alternatively, a separate ablation catheter may be introduced into the heart to operate in cooperation with the catheter of the invention.

In order that the signals are sensed properly by the pair of bipolar point electrodes (20, 22, 24, 26), in a preferred embodiment the shortest distance from the conventional tip electrode (16) to the most distal point electrode (24) is at least about 3 mm. (0.12 inch) and preferably from about 3 to about 5 mm. (0.12 to 0.19 inch).

Other conventional components may be secured to the catheter body including temperature sensing devices such as thermocouples or thermistors. In addition, the catheter may be steerable using conventional steering systems.

In operation, a modified Seldinger technique is normally used for the insertion of the catheter (10) into the body. Using this procedure, a small skin incision is made at the appropriate location to facilitate the catheter (10) or dilator passage. Subcutaneous tissue is then dissected, followed by a puncture of the vessel with an appropriate needle with stylet positioned at a relatively shallow angle. The needle is then partially withdrawn and reinserted at a slightly different angle into the vessel making sure that the needle remains within the vessel. The soft flexible tip of an appropriate size guidewire is then inserted through, and a short distance beyond, the needle into the vessel. Firmly holding the guidewire in place, the needle is removed. The guidewire is then advanced through the vessel into the appropriate vessel. With the guidewire in place, the dilator is then placed over the guidewire with an introducer placed over the dilator. The dilator and the introducer generally form an assembly to be advanced together along the guidewire into the heart. After insertion of the assembly, the guidewire is then withdrawn.

Once the introducer is in place, the catheter (10) containing point electrodes (20, 22, 24, 26) is advanced through the introducer into the heart for the sensing procedure. The point electrodes (20, 22, 24, 26) are then placed near or on the surface of the cardiac tissue and are activated to sense the general direction from which the activation wave of the arrhythmia focus is generated. By repeating this sensing activity within the chamber of the heart as needed, the pair of bipolar sensing electrode pairs can determine the approximate location of the arrhythmia focus. The tip electrode (16) may then be utilized in combination with an extracardiac electrode (not shown) in a unipolar mode to precisely locate the source of the arrhythmia focus. Once this source is determined, the tip electrode (16) is then utilized as an ablation electrode to ablate the arrhythmia focus. Alternatively, a separate ablation catheter may be utilized to ablate the arrhythmia focus.

By use of the catheter with pair of bipoles, the distal portion of the appropriate catheter can be manipulated to the correct location within the heart. By precisely locating the catheter in the heart, there will be no dilution of the energy delivered due to the unfocused energy being dissipated over the entire cardiac chamber and lost in the circulating blood by a constantly moving tip of the ablating catheter. This permits a significantly reduced amount of energy to be applied during the ablation procedure. Further, time used to perform the procedure is significantly reduced over procedures where conventional electrodes are used. In addition, by this ablation procedure the same types of destruction of the discrete location can be achieved as have been accomplished, for example, in previous surgical procedures.

It will be apparent from the foregoing that while particular forms of the invention have been illustrated and described, various modifications can be made without departing from the spirit and scope of the invention. Accordingly, it is not intended that this invention be limited except as by the appended claims.

What is claimed is:

1. A catheter for sensing electrophysiological activity within a human heart comprising an elongated catheter body having a distal tip, first and second point electrodes, which are secured to the elongated catheter body, comprising a first bipolar pair of electrodes, and third and fourth point electrodes, which are secured to the catheter body, comprising a second bipolar pair of electrodes, wherein a line passing between the third and fourth point electrodes is within about 45 degrees of being perpendicular to a line passing through the first and second point electrodes and wherein each of the point electrodes is generally circular in shape with a diameter from about 0.1 mm. (0.004 inch) to about 2.0 mm. (0.08 inch).

2. The catheter of claim 1 wherein the line passing between the third and fourth point electrodes is within about 30 degrees of being perpendicular to the line passing between the first and second point electrodes.

3. The catheter of claim 1 wherein the line passing between the third and fourth point electrodes is within about 10 degrees of being perpendicular to the line passing between the first and second point electrodes.

4. The catheter of claim 1 wherein the third point electrode is secured at a position on the catheter which is more distal from the proximal end of the catheter body than is the fourth point electrode.

5. The catheter of claim 1 wherein the third point electrode is secured at a position on the catheter body that is more distal from the proximal end of the catheter body than is the second point electrode.

6. The catheter of claim 1 wherein the fourth point electrode is secured at a position on the catheter body that is more proximal from the proximal end of the catheter body than is the second point electrode.

7. A catheter for sensing electrophysiological activity within a human heart comprising an elongated catheter body having a distal tip, first and second point electrodes, which are secured to the elongated catheter body, comprising a first bipolar pair of electrodes, and third and fourth point electrodes, which are secured to the catheter body, comprising a second bipolar pair of electrodes, wherein a line passing between the third and fourth point electrodes is within about 45 degrees of being perpendicular to a line passing through the first and second point electrodes wherein the first, second, third and fourth point electrodes form a generally diamond- shape on the catheter body.

8. The catheter of claim 1 wherein the distance between the first and fourth point electrodes and between the second and third point electrode is within about 2.0 mm. (0.08 inch) of being equal.

9. The catheter of claim 1 wherein the distance between the first and second point electrode is from about 0.5 mm. (0.02 inch) to about 3.0 mm. (0.12 inch).

10. The catheter of claim 1 further comprising a unipolar distal tip electrode secured to the distal end of the catheter body.

11. The catheter of claim 10 wherein the shortest distance between the unipolar distal tip electrode and the distal-most point electrode is from about 3.0 mm. (0.12 inch) to about 5.0 mm. (0.2 inch).

12. The catheter of claim 1 wherein the first and second point electrode bipoles are operably interfaced with conventional differential receiving and processing equipment to provide directional vectors to the electrophysiological activity of the human heart.

13. The catheter of claim 10 further comprising one or more ring electrodes secured to the catheter body.

14. A catheter for sensing electrophysiological activity within a human heart comprising an elongated catheter body having a distal tip, a first and second point electrodes which are secured to the elongated catheter body comprising a first bipolar pair of electrodes, and a third point electrode, wherein the third point electrode and the second point electrode comprise a second bipolar pair of electrodes and wherein each of the point electrodes is generally circular in shape with a diameter from about 0.1 mm. (0.004 inch) to about 2.0 mm. (0.08 inch).

15. The catheter of claim 14 wherein the first point electrode is secured to the catheter body at a position more proximal from the proximal end of the catheter body than is the third point electrode.

16. The catheter of claim 15 wherein the second point electrode is secured to the catheter body at a position more proximal to the proximal end of the catheter than is the third point electrode.

17. The catheter of claim 14 wherein the distance between the first and second point electrodes is from about 0.5 mm. (0.02 inch) to about 3.0 mm. (0.12 inch).

18. The catheter of claim 14 further comprising a unipolar distal tip electrode secured to the distal tip of the catheter body.

19. The catheter of claim 14 wherein the shortest distance between the unipolar distal tip electrode and the distal-most point electrodes is from about 3.0 mm. (0.12 inch) to about 5.0 mm. (0.2 inch).

20. The catheter of claim 14 wherein a line extending from the third point electrode through the second point electrode is within about 45 degrees of being perpendicular to the line passing between the first and second point electrodes.

21. The catheter of claim 14 wherein a line extending from the third point electrode through the second point electrode is within about 30 degrees of being perpendicular to the line passing between the first and second point electrodes.

22. The catheter of claim 14 wherein a line extending from the third point electrode through the second point electrode is within about 10 degrees of being perpendicular to the line passing between the first and second point electrodes.

23. A process for treatment of an arrhythmia focus within a human heart comprising introducing a sensing catheter within a chamber of the heart, wherein the catheter comprises a catheter body having a distal tip, a first and second point electrodes, which are secured to the catheter body and comprise a first bipolar pair of electrodes, and third and fourth point electrodes, which are secured to the catheter body and comprise a second bipolar pair of electrodes, wherein a line passing between the third and fourth point electrodes is within about 45 degrees of being perpendicular to a line passing through the first and second point electrodes, wherein each of the point electrodes is generally circular in shape with a diameter from about 0.1 mm. (0.004 inch) to about 2.0 mm. (0.08 inch), and sensing the general direction within the heart from which activation waves of the arrhythmia focus are generated utilizing the catheter with the pair of bipolar pairs of electrodes.

\* \* \* \* \*

UNITED STATES PATENT AND TRADEMARK OFFICE
CERTIFICATE OF CORRECTION

PATENT NO. : 6,466,811 B1  Page 1 of 1
DATED : October 15, 2002
INVENTOR(S) : James A. Hassett It is certified that error appears in the above-identified patent and that said Letters Patent is hereby corrected as shown below:

<u>Title page,</u>
Item [56], References Cited, U.S. PATENT DOCUMENTS, should be amended to include the following additional patents:

|  | U.S. PATENT DOCUMENTS |  |
|---|---|---|
| -- 4,649,924 A | 3/1987 | Taccardi |
| 4,660,571 A | 4/1987 | Hess |
| 4,945,912 A | 8/1990 | Langberg |
| 5,215,103 A | 6/1993 | Desai |
| 5,391,194 A | 2/1995 | Goldreyer |
| 5,398,683 A | 3/1995 | Edwards |
| 6,093,157 A | 7/2000 | Chandrasekaran -- |

FOREIGN PATENT DOCUMENTS, include the following:

-- WO    WO92/21285    12/1992 --

Signed and Sealed this

Eighth Day of July, 2003

JAMES E. ROGAN
*Director of the United States Patent and Trademark Office*